(12) United States Patent
Teng et al.

(10) Patent No.: US 6,320,047 B1
(45) Date of Patent: Nov. 20, 2001

(54) SUBSTITUTED ARYL OR HETEROARYLAMIDES HAVING RETINOID-LIKE BIOLOGICAL ACTIVITY

(75) Inventors: Min Teng, Aliso Viejo; Tien T. Duong, Irvine; Roshantha A. Chandraratna, Mission Viejo, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/829,310

(22) Filed: Apr. 9, 2001

Related U.S. Application Data

(62) Division of application No. 09/550,744, filed on Apr. 17, 2000, now Pat. No. 6,245,786, which is a division of application No. 09/215,509, filed on Dec. 17, 1998, now Pat. No. 6,051,713, which is a division of application No. 08/820,792, filed on Mar. 19, 1997, now Pat. No. 5,917,048, which is a division of application No. 08/561,999, filed on Nov. 22, 1995, now Pat. No. 5,663,357.

(51) Int. Cl.$^7$ .................... C07D 213/02; C07D 401/02; C07D 403/02

(52) U.S. Cl. .................... 544/238; 544/333; 546/269.7; 546/271.4; 546/275.1; 546/275.4; 546/309

(58) Field of Search ................ 544/238.333; 546/275.1, 546/275.4, 271.4, 269.7, 309

(56) References Cited

U.S. PATENT DOCUMENTS

| | | | |
|---|---|---|---|
| 4,096,341 | 6/1978 | Frazer | 560/85 |
| 4,220,646 | 9/1980 | Cotrel et al. | 424/250 |
| 4,258,052 | 3/1981 | Yu et al. | 424/266 |
| 4,261,730 | 4/1981 | Bollinger et al. | 71/94 |
| 4,326,055 | 4/1982 | Loeliger | 548/237 |
| 4,391,731 | 7/1983 | Boller et al. | 252/299.26 |
| 4,539,154 | 9/1985 | Krebs | 260/410 |
| 4,560,549 | 12/1985 | Ritchev | 424/18 |
| 4,695,649 | 9/1987 | Magami et al. | 560/86 |
| 4,723,028 | 2/1988 | Shudo | 560/8 |
| 4,739,098 | 4/1988 | Chandraratna | 514/461 |
| 4,740,519 | 4/1988 | Shrool et al. | 514/443 |
| 4,810,804 | 3/1989 | Chandraratna | 546/269 |
| 4,826,969 | 5/1989 | Maignan et al. | 536/55.2 |
| 4,826,984 | 5/1989 | Berlin et al. | 546/134 |
| 4,855,320 | 8/1989 | Chatterjee et al. | 514/473 |
| 4,895,868 | 1/1990 | Chandraratna | 546/165 |
| 4,927,947 | 5/1990 | Chandraratna | 549/484 |
| 4,980,369 | 12/1990 | Chandraratna | 514/314 |
| 4,992,468 | 2/1991 | Chandraratna | 549/484 |
| 5,006,550 | 4/1991 | Chandraratna | 549/23 |
| 5,013,744 | 5/1991 | Chandraratna | 514/354 |
| 5,015,658 | 5/1991 | Chandraratna | 514/337 |
| 5,023,341 | 6/1991 | Chandraratna | 514/256 |
| 5,037,825 | 8/1991 | Klaus et al. | 514/233.8 |
| 5,045,551 | 9/1991 | Chandraratna | 514/448 |
| 5,053,523 | 10/1991 | Chandraratna | 514/252 |
| 5,068,252 | 11/1991 | Chandraratna | 514/252 |
| 5,089,509 | 2/1992 | Chandraratna | 564/163 |
| 5,130,335 | 7/1992 | Chandraratna | 514/252 |
| 5,134,159 | 7/1992 | Chandraratna | 514/252 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |

(List continued on next page.)

FOREIGN PATENT DOCUMENTS

| | | | |
|---|---|---|---|
| 3305569 | 8/1984 | (DE) . | |
| 3708060 | 9/1987 | (DE) . | |
| 3715955 | 11/1987 | (DE) | C07C/15/58 |
| 3602473 | 7/1987 | (DE) | C07C/43/215 |

(List continued on next page.)

OTHER PUBLICATIONS

A General Synthesis of Terminal and Internal Arylalkynes by the Palladium–Catalyzed Reaction of Alkynylzine Reagents with Aryl Halides by Anthony O. King and Ei–i–chi, Negishi, *J. Org. Chem.,* (1978) 43/2: p. 358.

Conversion of Methyl Ketones into Terminal Acetylenes and (E)–Tri–substituted Olefins of Terpenoid Origin by Ei–ichi, et al., *J. Org. Chem.,* (1980) 45/12: p. 2526.

Sporn et al. in *J. Amer. Acad. Derm.,* (1986) 15:756–764.

"A Convenient Synthesis of Ethynylarenes and Diethynylarenes" by S. Takahashi et al. *Synthesis* (1980) pp. 627–630.

Shudo et al. in *Chem. Phar. Bull.,* (1985) 33:404–407.

Kagechika et al. in *J. Med. Chem.,* (1988) 31:2182–2192.

(List continued on next page.)

*Primary Examiner*—Zinna Northington Davis

(74) *Attorney, Agent, or Firm*—Gabor L. Szekeres; Robert J. Baran; Martin A. Voet

(57) ABSTRACT

Compounds of the formula wherein the symbols have the meaning described in the specification, have retinoid-like biological activity.

13 Claims, No Drawings

U.S. PATENT DOCUMENTS

| | | | |
|---|---|---|---|
| 5,354,752 | 10/1994 | Chandraratna | 514/252 |
| 5,354,776 | 10/1994 | Chandraratna | 514/461 |
| 5,380,877 | 1/1995 | Chandraratna | 549/60 |
| 5,391,753 | 2/1995 | Chandraratna | 546/323 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraratna | 514/365 |
| 5,420,145 | 5/1995 | Shudo | 514/352 |
| 5,426,118 | 6/1995 | Chandraratna | 514/337 |
| 5,434,173 | 7/1995 | Chandraratna | 514/354 |
| 5,451,605 | 9/1995 | Chandraratna et al. | 514/475 |
| 5,455,265 | 10/1995 | Chandraratna | 514/448 |
| 5,466,861 | 11/1995 | Dawson et al. | 560/100 |
| 5,468,879 | 11/1995 | Chandraratna | 549/23 |
| 5,470,999 | 11/1995 | Chandraratna | 560/100 |
| 5,475,022 | 12/1995 | Chandraratna | 514/448 |
| 5,475,113 | 12/1995 | Chandraratna | 548/203 |
| 5,489,584 | 2/1996 | Vuligonda et al. | 514/188 |
| 5,498,755 | 3/1996 | Chandraratna et al. | 564/272 |
| 5,498,795 | 3/1996 | Song et al. | 562/494 |
| 5,514,825 | 5/1996 | Vuligonda et al. | 558/462 |
| 5,516,904 | 5/1996 | Chandraratna | 514/269 |
| 5,523,457 | 6/1996 | Starrett, Jr. et al. | 560/24 |
| 5,534,516 | 7/1996 | Chandraratna | 514/253 |
| 5,534,641 | 7/1996 | Song et al. | 549/416 |
| 5,543,534 | 8/1996 | Vuligonda et al. | 549/421 |
| 5,556,996 | 9/1996 | Beard et al. | 549/407 |
| 5,559,248 | 9/1996 | Starrett, Jr. et al. | 549/79 |
| 5,563,292 | 10/1996 | Sheh et al. | 560/255 |
| 5,591,858 | 1/1997 | Vuligonda et al. | 546/322 |
| 5,599,819 | 2/1997 | Chandraratna | 514/314 |
| 5,599,967 | 2/1997 | Vuligonda et al. | 560/48 |
| 5,602,130 | 2/1997 | Chandraratna | 514/247 |
| 5,602,135 | 2/1997 | Chandraratna | 514/252 |
| 5,605,915 | 2/1997 | Vuligonda et al. | 514/356 |
| 5,616,597 | 4/1997 | Chandraratna | 514/365 |
| 5,616,712 | 4/1997 | Teng et al. | 546/158 |
| 5,618,836 | 4/1997 | Chandraratna et al. | 514/444 |
| 5,618,931 | 4/1997 | Beard et al. | 544/224 |
| 5,618,943 | 4/1997 | Vuligonda et al. | 546/342 |
| 5,663,357 | 9/1997 | Teng et al. | 546/323 |
| 6,051,713 | 4/2000 | Teng et al. | 546/262 |

FOREIGN PATENT DOCUMENTS

| | | | |
|---|---|---|---|
| 3316932 | 11/1983 | (DE) | C07C/63/66 |
| 3524199 | 1/1986 | (DE) | C07C/63/66 |
| 0098521 | 1/1984 | (EP) . | |
| 0130795 | 1/1985 | (EP) . | |
| 170105A | 1/1985 | (EP) . | |
| 0176032 | 4/1986 | (EP) . | |
| 0176033 | 4/1986 | (EP) . | |
| 0253302 | 1/1988 | (EP) . | |
| 0272921 | 6/1988 | (EP) . | |
| 0284288 | 9/1988 | (EP) . | |
| 0286364 | 10/1988 | (EP) . | |
| 0303186 | 2/1989 | (EP) . | |
| 0303915 | 2/1989 | (EP) . | |
| 176034A | 4/1989 | (EP) . | |
| 0315071 | 5/1989 | (EP) . | |
| 0350846 | 7/1989 | (EP) . | |
| 0619116 | 10/1994 | (EP) . | |
| 0718285 | 8/1996 | (EP) . | |
| 0661259 | 5/1995 | (EP) | C07C/233/81 |
| 0661261 | 7/1995 | (EP) | C07C/235/84 |
| 0412387 | 2/1991 | (EP) | C07C/317/14 |
| 0284261 | 9/1988 | (EP) | C07D/213/80 |
| 0617020 | 9/1994 | (EP) | C07D/213/82 |
| 0661258 | 7/1995 | (EP) | C07D/65/19 |
| 2190378 | 11/1987 | (GB) | C07C/39/21 |
| 6-72866 | 3/1994 | (JP) . | |
| 85/00806 | 2/1985 | (WO) . | |
| 85/04652 | 10/1985 | (WO) . | |
| 91/16051 | 10/1991 | (WO) . | |
| 93/11753 | 6/1993 | (WO) . | |
| 95/04036 | 2/1995 | (WO) . | |
| 96/05165 | 2/1996 | (WO) . | |
| 93/21146 | 10/1993 | (WO) | C07C/69/76 |
| 92/06948 | 4/1992 | (WO) | C07C/69/86 |

OTHER PUBLICATIONS

Chemistry and Biology of Synthetic Retinoids by Marcia I. Dawson and William H. Okamura, published by CRC Press Inc., 1990, pp. 334–335, 354.

Synthesis of 2,2'–Dineyl–1,1'–Biaryls. Regiocontrolled Protection of . . . by Mervic, et al, *J. Org. Chem.*, (1980) No. 45, pp. 4720–4725.

A Dopamine Receptor Model and Its Application in the Design of a New Class of Rigid Pyrrolo|2,3–g|isoquinoline Antipsychotics, Gary L. Olson et al. *American Chemical Societe,* (1981) 24/9:1026–1031.

6.2.3 Conformational Restriction, Williams, et al., *Drug Discovery and Development,* The Humana Press, (1987) pp. 54–55.

V. Retinoid Structure–Biological Activity Relationships, Chemistry and Biology of Synthetic Retinoids, (1990) pp. 324–356.

Davis et al. *J. Organomettalic Chem* (1990) 387:381–390.

"Effects of 13–Cis–Retinoic Acid, All Trans–Retinoic Acid, and Acitretin on the Proliferation, Lipid Synthesis and Keratin Expression of Cultured Human Sebocytes in Vitro" C.C. Zouboulis, *The Journal of Investigative Dermatology,* (1991) 96/5:792–797.

"Organ Maintenance of Human Sebaceous Glands: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology,* (1991) 96/3:.

"Synthesis and Evaluation of Stilbene and Dihydrostilbene Derivateives as Potential Anticancer Agents That Inhibit Tubulin Polymerization" by Cushman, Mark et al. *J. Med. Chem.,* (1991), 34:2579–2588.

"Synthesis and Evaluatinof New Protocin Tyrosine Kinase Inhibitors. Part I. Pyridine–Containing Stilbenes and Amides" by Cushman, Mark et al. *Bioorganic & Medicinal Chemistry Letters,* (1991) 1/4:211–214.

"Di– and Tri–methoxystyryl Derivatives of Heterocyclic Nitrogen Compounds" by Bahner,C. T. et al. *Arzneim–Forsch./Drug Res,* (1981)31 (1), Nr. 3.

"Retinobenzoic acids. 3. Structure–Activity Relationships of Retinoidal Azobenzene–4–Carboxylic Acids and Stilbene–4– Carboxylic Acids" by H. Kagechika et al., *Journal of Medicinal Chemistry,* (1989), 32:1098–1108.

Eyrolles, L. et al. "Retinoid Antagonists: Molecular Design Based on the Ligand Superfamily Concept" *Med. Chem. Res.,* (1992) 2:361–367.

Liu, S. S. et al. "Systemic Pharmacokinetics of Acetylenic Retinoids in Rats", *Drug Metabolism and Disposition,* (1990) 18/6: 1071–1077.

Chemical Abstracts, vol. 122, No. 13, Mar. 27, 1995 abstract No. 151372m, (S. Kaku et al.).

Chemical Abstracts, vol. 117, No. 13, Sep. 28, 1992 abstract No. 124091j, (S. Sun et al.).

European Journal of Biochemistry, vol. 212, No. 1, 1993, Berlin, pp. 13–26, XP000618300 (S. Keidel et al.).

Journal of Medicinal Chemistry, vol. 39, No. 16, Aug. 2, 1996, pp. 3035–3038, Min Teng et al.

Journal of Medicinal Chemistry, vol. 37, No. 10, May 13, 1994, pp. 1508–1517, Laurence Eyrolles.

Biochemical and Biophysical Research Communications, vol. 155 No. 1, 1988, pp. 503–508.

SUBSTITUTED ARYL OR HETEROARYLAMIDES HAVING RETINOID-LIKE BIOLOGICAL ACTIVITY

CROSS-REFERENCE TO RELATED APPLICATION

This application is a divisional of application Ser. No. 09/550,744, filed on Apr. 17, 2000, to be issued as U.S. Pat. No. 6,245,786, which is a divisional of application Ser. No. 09/215,509, filed on Dec. 17, 1998 now U.S. Pat. No. 6,051,713, which is a divisional application Ser. No. 08/820,792, filed on Mar. 19, 1997, now issued as U.S. Pat. No. 5,917,048, which is itself a divisional of application Ser. No. 08/561,999, filed on Nov. 22, 1995, now U.S. Pat. No. 5,663,357.

BACKGROUND OF THE INVENTION

1. Field of the Invention

The present invention relates to novel compounds having retinoid-like biological activity. More specifically, the present invention relates to amides formed between aryl or heteraryl amines and aryl or heteroaryl carboxylic acids where one of the aromatic or heteroaromatic moieties bears an electron withdrawing substituent. The compounds have retinoid-like biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T- Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

U.S. Pat. No. 4,723,028 (Shudo), Published European Patent Application Nos. 0 170 105 (Shudo), German Patent Application No. DE 3524199 A1 (Shudo), PCT WO 91/16051 (Spada et al.), PCT WO 85/04652 (Polus) and J. Med Chem. 1988 31, 2182–2192 (Kapechika et al.), describe or relate to aryl and heteroary or diary substituted olephines or amides having retinoid-like or related biological activity.

U.S. Pat. Nos. 4,992,468, 5,013,744, 5,068,252, 5,175,185, 5,202,471, 5,264,456, 5,324,840, 5,326,898, 5,349,105, 5,391,753, 5,414,007 and 5,434,173 (assigned to the same assignee as the present application) and patents and publications cited therein, describe or relate to compounds which have retinoid-like biological activity and a structure wherein a phenyl and a heteroaryl or a phenyl and a second phenyl group is linked with an olephinic or acetylenic linkage. Still further, several co-pending applications and recently issued patents which are assigned to the assignee of the present application, are directed to further compounds having retinoid-like activity.

It is now general knowledge in the art that two main types of retinoid receptors exist in mammals (and other organisms). The two main types or families of receptors are respectively designated RARs and RXRs. Within each type there are subtypes; in the RAR family the subtypes are designated $RAR_\alpha$, $RAR_\beta$ and $RAR_\Gamma$, in RXR the subtypes are: $RXR_\alpha$, $RXB_\beta$ and $RXR_\Gamma$. It has also been established in the art that the distribution of the two main retinoid receptor types, and of the several sub-types is not uniform in the various tissues and organs of mammalian organisms. Accordingly, among compounds capable of binding to retinoid receptors, specificity or selectivity for one of the main types or families, and even specificity or selectivity for one or more subtypes within a family of receptors, is considered a desirable pharmacological property.

The present invention provides compounds having retinoid-like biological activity and specifically compounds which bind to one or more RAR retinoid receptor subtypes.

SUMMARY OF THE INVENTION

The present invention covers compounds of Formula

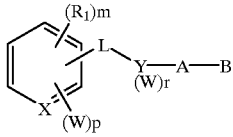

Formula I wherein X is CH or N;

$R_1$ is independently H or alkyl of 1 to 6 carbons;

m is an integer having the value of 0–5;

p is an integer having the value of 0–2;

r is an integer having the value 0–2;

L is —(C=Z)—NH— or —NH—(C=Z)— where S is O or S;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being optionally substituted with one or two $R_1$ groups;

W is a substituent selected from the group consisting of F, Br, Cl, I, $C_{1-6}$alkyl, fluoro substituted $C_{1-6}$ alkyl, $NO_2$, $N_3$, OH, $OCH_2OCH_3$, $OC_{1-10}$alkyl, tetrazol, CN, $SO_2C_{1-6}$-alkyl, $SO_2C_{1-6}$-alkyl, $SO_2C_{1-6}$-fluoro substituted alkyl, $SO$-$C_{1-6}$ alkyl, $CO$-$C_{1-6}$alkyl, $COOR_8$, phenyl, phenyl itself substituted with a W group other than with phenyl or substituted phenyl with the proviso that when X is CH and r is O then p is not 0 and at least one W group is not alkyl;

A is $(CH_2)$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of cancerous and precancerous conditions, including, pre-malignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreo-retinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

This invention also relates to a pharmaceutical formulation comprising a compound of Formula 1 in admixture with a pharmaceutically acceptable excipient.

In another aspect, this invention relates to processes for making a compound of Formula 1 which processes comprise reacting, in the presence of an acid acceptor or water acceptor, a compound of Formula 2 with a compound of Formula 3 where $X_1$ is OH, halogen, or other group which renders the —COX, group reactive for amide formation, and where the remaining symbols are defined as in connection with Formula 1. Alternatively, the process of the invention comprises reacting a compound of Formula 2a with a compound of Formula 3a, where the symbols are defined as above.

Formula 2

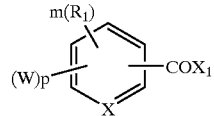

Formula 3

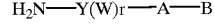

Formula 2a

Formula 3a

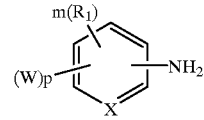

Still further, the present invention relates to such reactions performed on the compounds of Formula 1 which cause transformations of the B group while the reaction product still remains within the scope of Formula 1.

General Embodiments

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thioalcohols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$, where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula—CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compounds in this invention having a functionality capable of forming such-salt, for example an acid functionality. A pharmaceutically acceptable salt is any salt which retains the activity of the parent compound and does not impart any deleterious or untoward effect on the subject to which it is administered and in the context in which it is administered. Pharmaceutically acceptable salts may be derived from organic or inorganic bases. The salt may be a mono or polyvalent ion. Of particular interest are the inorganic ions, sodium, potassium, calcium, and magnesium. Organic salts may by be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some of the compounds of the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

With reference to the symbol X in Formula 1, compounds are equally preferred where X is CH or N. When X is CH then the benzene ring is preferably 1, 3, 5 substituted with the L group occupying the 1 position and the W and/or R$_1$ groups occupying the 3 and 5 positions. When the symbol X is N, then the pyridine ring is preferably 2,4,6 substituted with the L group occupying the 4 position and the W and/or R$_1$ groups occupying the 2 and 6 positions.

The L group of Formula 1 is preferably —(C=Z)—NH—, and Z is preferably O. In other words, those carbamoyl or amide compounds are preferred in accordance with the present invention where the —NH-moiety is attached to the Y group.

Referring now to the W group in Formula 1, this group is, generally speaking, an electron withdrawing group. W is present in the compounds of the invention either in the phenyl or pyridyl ring (shown in Formula 1 as substituent "(W)$_p$") and/or as a substituent of the aryl or heteroaryl group Y. Preferably, the W group is present in the Y group, or both in the Y group and in the phenyl or pyridyl ring discussed above. In the aryl or heteroaryl Y moiety the W group is preferably located in the position adjacent to the A–B group; preferably the A–B group is in para position in the phenyl ring relative to the L (amide or carbamoyl) moiety, and therefore the W group is preferably in meta position relative to the L (amide or carbamoyl) moiety. Preferred W groups are F, NO$_2$, Br, I, CF$_3$, N$_3$, and OH. Alternatively, in the phenyl or pyridyl ring (shown in Formula 1 as substituent "(W)$_p$") W is an alkyl group, preferably branch-chained alkyl, such as tertiary butyl, and preferably p is 2. Moreover, the presence of one or two fluoro substituents in the Y group is especially preferred. When the Y group is phenyl, the fluoro substituents preferably are in the ortho and ortho' positions relative to the A–B group.

With reference to the symbol Y in Formula 1, the preferred compounds of the invention are those where Y is phenyl, pyridyl, 2-thiazolyl, thienyl, or furyl, more preferably phenyl. As far as substitutions on the Y (phenyl) and Y (pyridyl) groups are concerned, compounds are preferred where the phenyl group is 1,4 (sara) substituted by the L and A–B groups, and where the pyridine ring is 2,5 substituted by the L and A–B groups. (Substitution in the 2,5 positions in the "pyridine" nomenclature corresponds to substitution in the 6-position in the "nicotinic acid" nomenclature.) In the preferred compounds of the invention there is no optional R$_1$ substituent (other than H) on the Y group.

The R$_1$ groups, when present, preferably are H or CH$_3$.

The A–B group of the preferred compounds is (CH$_2$)$_n$—COOH or (CH$_2$)$_n$—COOR$_8$, where n and R$_8$ are defined as above. Even more preferably n is zero and R$_8$ is lower alkyl, or n is zero and B is COOH or a pharmaceutically acceptable salt thereof.

The most preferred compounds of the invention are shown in Table 1, with reference to Formula 4.

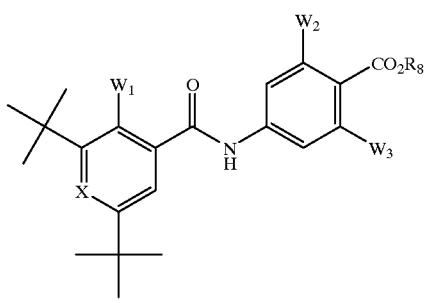

Formula 4

TABLE 1

| Compound # | X | $W_1$ | $W_2$ | $W_3$ | $R_8$* |
|---|---|---|---|---|---|
| 1 | N | H | F | H | Et |
| 2 | N | H | F | H | H |
| 3 | N | H | H | H | Et |
| 4 | N | H | H | H | H |
| 5 | CH | H | F | H | Et |
| 6 | CH | H | F | H | H |
| 7 | CH | OH | F | H | Et |
| 8 | CH | OH | F | H | H |
| 9 | N | H | F | F | Me |
| 10 | N | H | F | F | H |
| 11 | CH | H | F | F | Me |
| 12 | CH | H | F | F | H |
| 13 | N | H | $NO_2$ | H | Me |
| 14 | N | H | $NO_2$ | H | H |
| 15[1] | CH | H | H | H | H |

[1]Compound 15 is prior art, described in J. Med Chem. 1988, 31, 2182 (Kagechika et al.)

Modes of Administration

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per mililiter of formulation will constitute a therapeutically effective concentration for total application. If administered systemically, an amount between 0.01 and 5 mg per kg per day of body weight would be expected to effect a therapeutic result in the treatment of many disease for which these compounds are useful.

Assay of Retinoid-like Biological Activity

The retinoid-like activity of the compounds of the invention can be confirmed in assays wherein ability of the compound to bind to retinoid receptors is measured. As it is noted in the introductory section of this application for patent two main types of retinoic acid receptors (RAR and RXR) exist in mammals (and other organisms). Within each type there are sub-types ($RAR_\alpha$, $RAR_\beta$, $RAR_\Gamma$, $RXR_\alpha$, $RXR_\beta$ and $RXR_\Gamma$) the distribution of which is not uniform in the various tissues and organs of mammalian organisms. Selective binding of only one or two retinoid receptor subtypes within one retinoid receptor family can give rise to beneficial pharmacological properties because of the varying distribution of the sub-types in the several mammalian tissues or organs. For the above-summarized reasons, binding of any or all of the retinoid receptors, as well as specific or selective activity in a receptor family, or selective or specific activity in any one of the receptor subtypes, are all considered desirable pharmacological properties.

In light of the foregoing the prior art has developed assay procedures for testing the agonist like activity of compounds in the $RAR_\alpha$, $RAR_\beta$, $RAR_\Gamma$, $RXR_\alpha$, $RXR_\beta$ and $RXR_\Gamma$ receptor subtypes. For example, a chimeric receptor transactivation assay which tests for agonist-like activity in the $RAR_\alpha$, $RAR_\beta$, $RAR_\Gamma$, and $RXR_\alpha$ receptor subtypes, and which is based on work published by Feigner P. L. and Holm M. (1989) Focus, 11 2 is described in detail in U.S. Pat. No. 5,455,265. The specification of U.S. Pat. No. 5,455,265 is expressly incorporated herein by reference.

A holoreceptor transactivation assay and a ligand binding assay which measure the ability of the compounds of the invention to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A description of the ligand binding assay is also provided below.

BINDING ASSAY

All binding assays were performed in a similar fashion. All six receptor types were derived from the expressed receptor type (RAR α, β, Γ and RXR α, β, Γ) expressed in Baculovirus. Stock solutions of all compounds were prepared as 10 mM ethanol solutions and serial dilutions carried out into 1:1 DMSO; ethanol. Assay buffers consisted of the following for all six receptor assays: 8% glycerol, 120 mM KCl, 8 mM Tris, 5 mM CHAPS 4 mM DTT and 0.24 mM PMSF, pH-7.4@ room temperature.

All receptor biding assays were performed in the same manner. The final assay volume was 250μl and contained from 10–40 μg of extract protein depending on receptor being assayed along with 5 mM of [$^3$H] all-trans retinoic acid or 10 nM [$^3$H] 9-cis retinoic acid and varying concentrations of competing ligand at concentrations that ranged from 0–10$^{-5}$ M. The assays were formatted for a 96 well minitube system. Incubations were carried out at 4° C. until equilibrium was achieved. Non-specific binding was defined as that binding remaining in the presence of 1000 nM of the appropriate unlabeled retinoic acid isomer. At the end of the incubation period, 50 μl of 6.25% hydroxyapitite was added in the appropriate wash buffer. The wash buffer consisted of 100 mM KCl, 10 mM Tris and either 5 mM CHAPS (RXR α, β, Γ) or 0.5% Triton X-100 (RAR α, β, Γ). The mixture was vortexed and incubated for 10 minutes at 4° C., centrifuged and the supernatant removed. The hydroxyapitite was washed three more times with the appropriate wash buffer. The receptor-ligand complex was adsorbed by the hydroxyapitite. The amount of receptor-ligand complex was determined by liquid scintillation counting of hydroxyapitite pellet.

After correcting for non-specific binding, $IC_{50}$ values were determined. The $IC_{50}$ value is defined as the concentration of competing ligand needed to reduce specific binding by 50%. The $IC_{50}$ value was determined graphically from a loglogit plot of the data. The $K_d$ values were determined by application of the Cheng-prussof equation to the $IC_{50}$ values, the labeled ligand concentration and the $K_d$ of the labeled ligand.

The results of ligand binding assay are expressed in $K_d$ numbers. (See Cheng et al. Biochemical Pharmacology Vol. 22 pp 3099–3108, expressly incorporated herein by reference.)

Table 2 shows the results of the ligand binding assay for certain exemplary compounds of the invention.

TABLE 2

Ligand Binding Assay $K_d$(nanomolar)

| Compound # | RARα | RARβ | RARΓ | RXRα | RXRβ | RXRΓ |
|---|---|---|---|---|---|---|
| 2 | 14.00 | 0.00 | 0.00 | 0.00 | 0.00 | 0.00 |
| 4 | 19.00 | 0.00 | 0.00 | 0.00 | 0.00 | 0.00 |
| 6 | 26.0 | 0.90 | 0.00 | 0.00 | 0.00 | 0.00 |
| 8 | 77.0 | 0.00 | 0.00 | 0.00 | 0.00 | 0.00 |
| 10 | 62.0 | 0.00 | 0.00 | 0.00 | 0.00 | 0.00 |
| 12 | 87.0 | 0.00 | 0.00 | 0.00 | 0.00 | 0.00 |
| 14 | 94.0 | 0.00 | 0.00 | 0.00 | 0.00 | 0.00 |
| 15[1] | 37.0 | 0.00 | 0.00 | 0.00 | 0.00 | 0.00 |

0.00 indicates value greater than 1000 nM
(nanomolar) [1]Compound 15 is prior art, described in J. Med Chem. 1988, 31, 2182 (Kagechikaetal.)

As it can be seen from the test results summarized in Table 2, the therein indicated exemplary compounds of the invention bind specifically or selectively to RARα receptors.

CANCER CELL LINE ASSAYS

MATERIALS AND METHODS

Hormones

All trans-Retinoic acid (t-RA) (Sigma Chemicals Co., St. Louis, Mo.) was stored at −70° C. Prior to each experiment the compound was dissolved in 100% ethanol at 1 mM and diluted in culture medium immediately before use. All experiments were performed in subdued light. Controls were assayed using the same concentration of ethanol as present in the experimental plates and this concentration of diluent had no effect in either assay.

Cells and Cell Culture

All cell lines, RPMI 8226, ME-180 and AML-193 were obtained from the American Type Culture Collection (ATCC, Rockville, Md.). RPMI 8226 is a human hematopoietic cell line obtained from the peripheral blood of a patient with multiple myeloma. The cells resemble the lymphoblastoid cells of other human lymphocyte cell lines and secrete α-type light chains of immunoglobulin. RPMI-8226 cells are grown in RPMI medium (Gibco) supplemented with 10% fetal bovine serum, glutamine and antibiotics. The cells were maintained as suspension cultures grown at 37° C. in a humidified atmosphere of 5% $CO_2$ in air. The cells were diluted to a concentration of 1×10$^5$/ml twice a week.

ME-180 is a human epidermoid carcinoma cell line derived from the cervix. The tumor was a highly invasive squamous cell carcinoma with irregular cell clusters and no significant keratinization. ME-180 cells were grown and maintained in McCoy's 5a medium (Gibco) supplemented with 10% fetal bovine serum, glutamine and antibiotics. The cells were maintained as monolayer cultures grown at 37° C in a humidified atmosphere of 5% $CO_2$ in air. The cells were diluted to a concentration of 1×10$^5$/ml twice a week.

AML-193 was established from the blast cells classified as M5 Acute Monocyte Leukemia. The growth factor, granulocyte colony-stimulation factor (GM-CSF) was required to establish this cell line and growth factors are necessary for its continuous proliferation in chemically defined medium. AML-193 cells were grown and maintained in Iscovels modified Dulbecco's medium supplemented with 10% fetal bovine serum, glutamine and antibiotics with 5 μg/ml insulin (Sigma Chemical Co.) and 2 ng/ml rh GM-CSF (R and D Systems). The cells were diluted to a concentration of 3×10$^5$/ml twice a week.

Incorporation of $^3$H-Thymidine

The method used for determination of the incorporation of radiolabeled thymidine was adapted from the procedure described by Shrivastav et al. RPMI-8226 cells were plated in a 96 well round bottom microtiter plate (Costar) at a density of 1,000 cells/well. To appropriate wells, retinoid test compounds were added at the final concentrations indicated for a final volume of 150 μl/well. The plates were incubated for 96 hours at 37° C. in a humidified atmosphere of 5% $CO_2$ in air. Subsequently, 1 μCi of [5'-$^3$H]-thymidine (Amersham, U.K. 43 Ci/mmol specific activity) in 25 μl culture medium was added to each well and the cells were incubated for an additional 6 hours. The cultures were further processed as described below.

ME-180 wells, harvested by trypsinization were plated in a 96 well flat bottom microtiter plate (Costar) at a density of 2,000 cells/well. The cultures were treated as described above for RPMI 8226 with the following exceptions. After incubation with thymidine the supernatant was carefully removed, and the cells were washed with a 0.5 mM solution of thymidine in phosphate buffered saline. ME180 cells were briefly treated with 50 μl of 2.5% trypsin to dislodge the cells from the plate.

AML-193 cells were plated in a 96 well round bottom microtiter plate (Costar) at a density of 1,000 cells/well. To appropriate wells, retinoid test compounds were added at the final concentrations indicated for a final volume of 150 µl/well. The plates were incubated for 96 hours at 37° C. in a humidified atmosphere of 5% $CO_2$ in air. Subsequently, 1 µCi of [5'-$^3$H]-thymidine (Amersham, U.K., 43 Ci/mmol specific activity) in 25 µl culture medium was added to each well and the cells were incubated for an additional 6 hours.

All cells lines were then processed as follows: the cellular DNA was precipitated with 10% trichloroacetic acid onto glass fiber filter mats using a SKATRON multi-well cell harvester (Skatron Instruments, Sterling Va.). Radioactivity incorporated into DNA, as a direct measurement of cell growth, was measured by liquid scintillation counting. The numbers represent the mean disintegrations per minute of incorporated thymidine from triplicate wells ±SEM.

In the above noted in vitro cell lines exemplary Compound 2 of the invention caused significant decrease in the proliferation of the tumor cell lines (as measured by incorporation of radioactive labeled thymidine) in the $10^{-11}$ to $10^{-6}$ molar concentration range of the test compound.

SPECIFIC EMBODIMENTS

The compounds of this invention can be made by the synthetic chemical pathways illustrated here. The synthetic chemist will readily appreciate that the conditions set out here are specific embodiments which can be generalized to any and all of the compounds represented by Formula 1.

Generally speaking the process of preparing compounds of the invention involves the formation of an amide by the reaction of a compound of the general Formula 2 with a compound of general Formula 3, or by the reaction of a compound of general Formula 2a with a compound of general Formula 3a as these formulas are defined in the Summary section of the present application for patent. Thus, as is noted above, a compound of Formula 2 is an acid or an "activated form" of a carboxylic acid attached to a substituted phenyl (in Formula 1 X is CH) or to a substituted pyridyl (in Formula 1 X is N) nucleus.

The term "activated form" of the carboxylic acid should be understood in this regard as such derivative of the carboxylic acid which is capable of forming an amide when reacted with a primary amine of Formula 3. In case of the "reverse amides" the activated form of a carboxylic acid is a derivative (Formula 3a) that is capable of forming an amide when reacted with a primary amine of Formula 2a. This, generally speaking, means such derivatives of a carboxylic acid which are normally known and used in the art to form amide linkages with an amine. Examples of suitable forms or derivatives for this purpose are acid chlorides, acid bromides, and esters of the carboxylic acid, particularly active esters, where the alcohol moiety of the ester forms a good leaving group. Presently most preferred as reagents in accordance with Formula 2 (or Formula 3a) are acid chlorides ($X_1$ is Cl). The acid chlorides of Formula 2 (or of Formula 3a) can be prepared by traditional methods from the corresponding esters ($X_1$ is for example ethyl) by hydrolysis and treatment with thionyl chloride ($SOCl_2$). The acid chlorides of Formula 2 (or of Formula 3a) can also be prepared by direct treatment of the carboxylic acids with thionyl chloride, where the carboxylic acid, rather than an ester thereof is available commercially or by a known synthetic procedure. The acid chlorides of Formula 2 (or of Formula 3a) are typically reacted with the amine of Formula 3 (or amine of Formula 2a) in an inert solvent, such as methylene chloride, in the presence of an acid acceptor, such as pyridine.

The carboxylic acids themselves in accordance with Formula 2 (or Formula 3a) are also suitable for amide formation when reacted with an amine, a catalyst (4-dimethylaminopyridine) in the presence of a dehydrating agent, such as dicyclohexylcarbodiimide (DCC) or more pereferably 1-(3-dimethylaminopropyl)-3-ethylcarbodiimide hydrochloride (EDC).

The carboxylic acids or the corresponding esters of Formula 2, are generally speaking, prepared as described in the chemical scientific or patent literature and the literature procedures for their preparation may be modified, if necessary, by such chemical reactions or processes which per se are known in the art. Reaction Scheme 1 provides an example for the preparation of 2,6-di-tert-butylisonicotinic acid (Compound C) which is a reagant in accordance with Formula 2 for the preparation of several preferred compounds of the present invention. Thus, 2,6-di-tert-butyl-4-methylpyridine (available commercially from Aldrich Chemical Co.) is reacted with N-bromosuccinimide and benzoyl peroxide to provide 4-bromomethyl-2,6-di-tert-butylpyridine (Compound A). Compound A is reacted with base (sodium hydroxyde) to yield the coresponding hydroxymethyl compound (Compound B), which is thereafter oxidized in a Jones oxydation reaction to give 2,6-di-tert-butylisonicotinic acid (Compound C).

Reaction Scheme 1

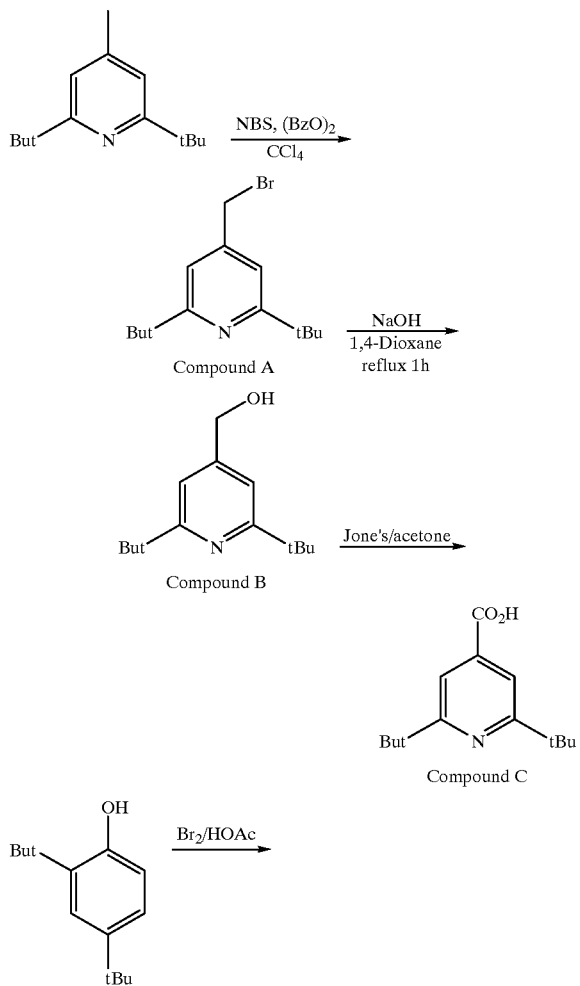

Reaction Scheme 2

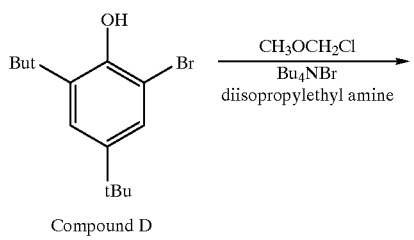

Compound D

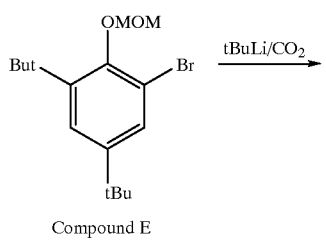

Compound E

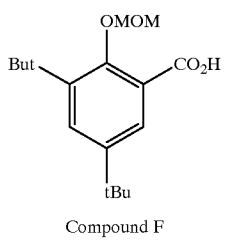

Compound F

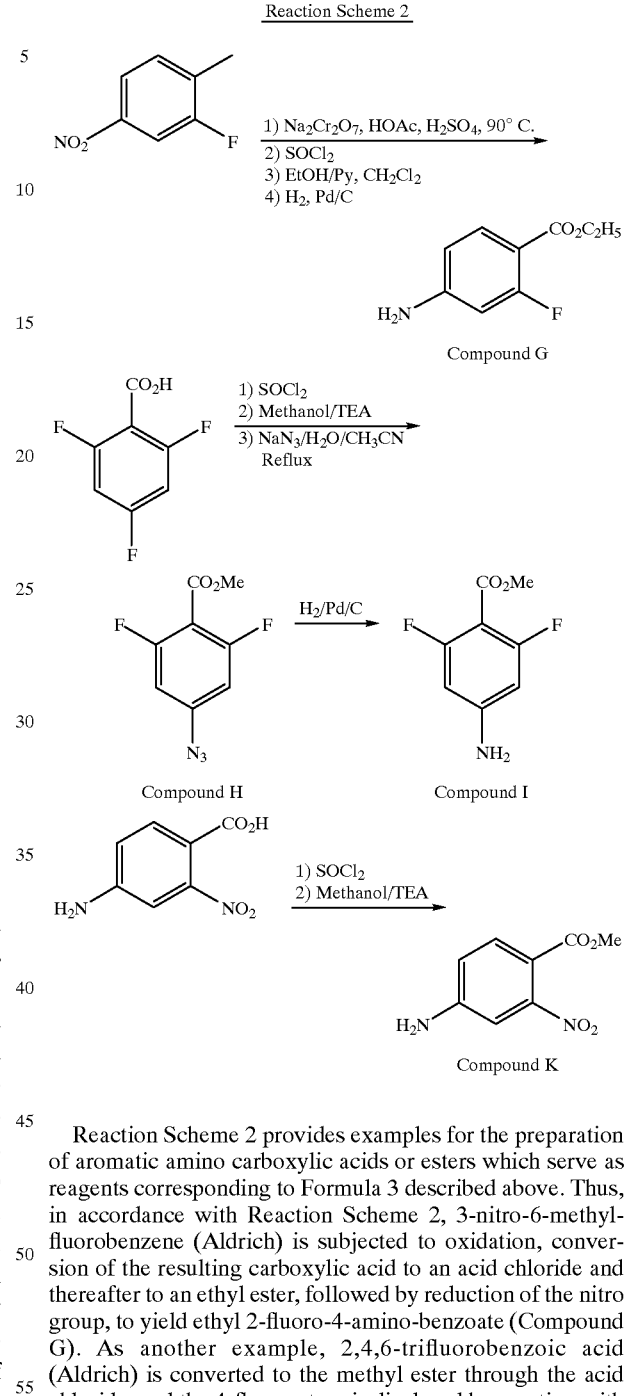

A further example of a compound which serves as a reagent for preparing the carbamoyl (or amide) compounds of the present invention is provided in Reaction Scheme 1. 2,4-Di-tert-butylphenol (Aldrich) is brominated in glacial acetic acid to yield 2-bromo-4,6-di-tert-butylphenol (Compound D) which is thereafter reacted with methoxymethyl chloride (MOMCl) to give O-methoxymethyl-2-bromo-4,6-di-tert-butylphenol (Compound E). Compound E is treated with t-butyl lithium followed by carbon dioxide to yield O-methoxymethyl-3,5-di-tert-butylsalicylic acid (Compound F). Compound F is a reagent which differs from the compounds generally encompassed by Formula 2 only in that the hydroxyl funtion of this compound is protected by the methoxymethyl (MOM) group. However, the methoxymethyl protecting group is removed after formation of the carbamoyl (amide) linkage, as exemplified in Reaction Scheme 5. Reaction of an aromatic bromo compound (such as Compound D) with t-butyl lithium followed by carbon dioxide is a preferred method for preparing several aromatic carboxylic acids in accordance with Formula 2 and Formula 3a, described in the present application.

Reaction Scheme 2 provides examples for the preparation of aromatic amino carboxylic acids or esters which serve as reagents corresponding to Formula 3 described above. Thus, in accordance with Reaction Scheme 2, 3-nitro-6-methyl-fluorobenzene (Aldrich) is subjected to oxidation, conversion of the resulting carboxylic acid to an acid chloride and thereafter to an ethyl ester, followed by reduction of the nitro group, to yield ethyl 2-fluoro-4-amino-benzoate (Compound G). As another example, 2,4,6-trifluorobenzoic acid (Aldrich) is converted to the methyl ester through the acid chloride, and the 4-fluoro atom is displaced by reaction with sodium azide to give the intermediate azido compound (Compound H). Compound H is reduced by hydrogenation, to yield methyl 2,6-difluoro-4-amino benzoate (Compound I). As still another example, 2-nitro-4-aminobenzoic acid (Research Plus Inc.) is converted to its methyl ester (Compound K) through the corresponding acid chloride.

Reaction Scheme 3

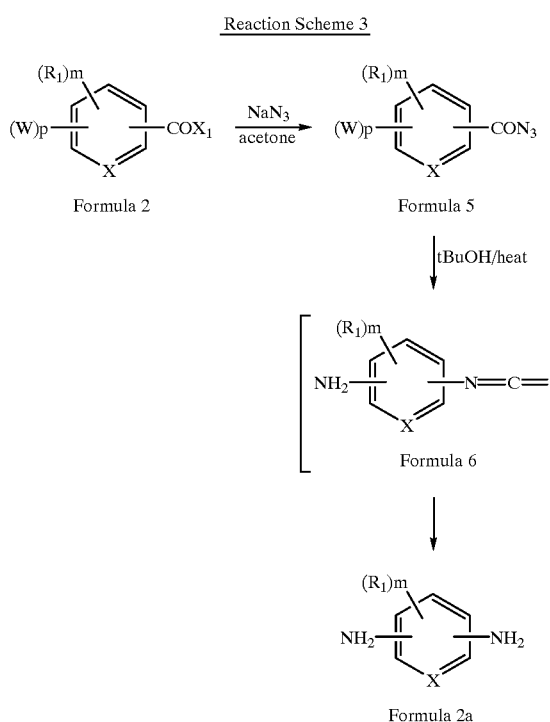

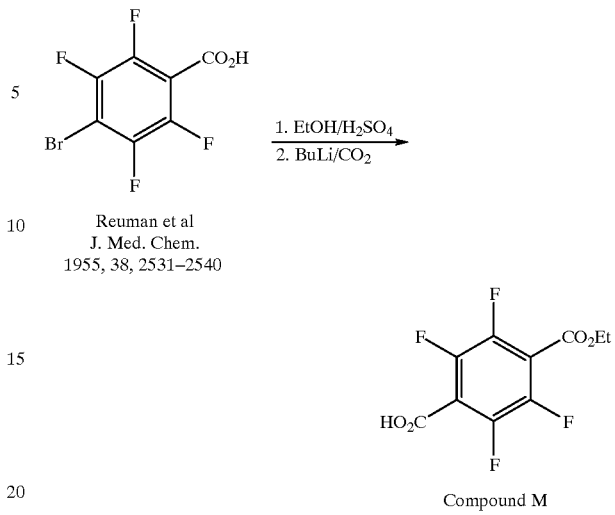

Reuman et al
J. Med. Chem.
1955, 38, 2531–2540

Compound M

Reaction Scheme 3 illustrates the synthesis of the primary amine compounds of Formula 2a from the acid chlorides ($X_1$=Cl) or other form of activated acids of Formula 2 where the primary amine of Formula 2a is not available by a published literature procedure. Thus, substantially in accordance with the steps of a Curtius rearrangement, the acid chloride of Formula 2 is reacted with sodium azide in acetone to yield the azide compound of Formula 5. The azide of Formula 5 is heated in a polar high boiling solvent, such as t-butanol, to provide the intermediate isocyanate of Formula 6, which is hydrolyzed to yield a compound of Formula 2a.

Reaction Scheme 4

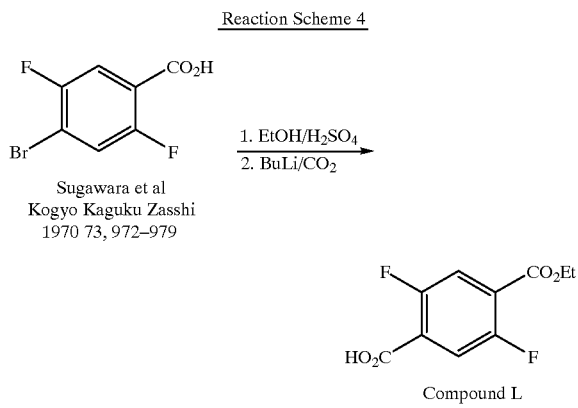

Sugawara et al
Kogyo Kaguku Zasshi
1970 73, 972–979

Compound L

Reaction Scheme 4 illustrates examples for preparing compounds of Formula 3a where such compounds are not available commercially or by a published literature procedure. Thus, by way of example 2,5-difluoro-4-bromobenzoic acid (available by the literature procedure of Sugawara et al. Kogyo Kaguku Zasshi 1970, 73, 972–979, incorporated herein by reference) is first esterified by treatment with ethyl alcohol and acid to yield the corresponding ester, and thereafter is reacted with butyl lithium followed by carbon dioxide to give the monoester of 2,5-difluoro terephthalic acid (Compound L). A similar sequence of reactions performed on 2,3,5,6-difluoro-4-bromobenzoic acid (available by the literature procedure of Reuman et al. J. Med. Chem. 1995, 38, 2531–2540, incorporated herein by reference) yields the monoester of 2,3,5,6-tetrafluoroterephthalic acid (Compound M) The just illustrated sequence of reactions can be, generally speaking, utilized for the synthesis of all compounds of Formula 3a with such modification which will become readily apparent to those skilled in the art, where such compounds are not available by a known literature procedure.

Numerous other reactions suitable for preparing compounds of the invention, and for converting compounds of Formula 1 within the scope of the present invention into still further compounds of the invention, and also for preparing the reagents of Formula 2, Formula 3, Formula 2a and Formula 3a will become readily apparent to those skilled in the art in light of the present disclosure. In this regard the following general synthetic methodology, applicable for conversion of the compounds of Formula 1 into further homologs and/or derivatives, and also for preparing the reagents of Formula 2 and 3, (as well as 2a and 3a) is noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced organic Chemistry," 2nd Edition, McGraw-Hill Book Company, p 810). Alcohols, aldehydes and ketones all may be protected by forming respectively, ethers and esters, acetals or ketals by known methods such as those described in Mcomie, Plenum Publishing Press, 1973 and *Protecting Groups,* Ed. Greene, John Wiley & Sons, 1981.

A means for making compounds where A is $(CH_2)_q$ (q is 1–5) is to subject the compounds of Formula 1, where B is an acid or other function, to homologation, using the well known Arndt-Eistert method of homologation, or other known homologation procedures. Similar homologations (and several of the other herein mentioned synthetic transformations) can be transformed on the reagents of Formula 3 or 3a. Compounds of the invention, where A is an alkenyl group having one or more double bonds can be made, for example, by having the requisite number of double bonds incorporated into the reagent of Formula 3. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halocarboxylic acid, ester or like carboxaldehyde. Compounds of the invention where the A group has a triple (acetylenic) bond can be made by using the corresponding aryl or heteroaryl aldehyde intermediate. Such intermediate can be obtained by reactions well known in the art, for example, by reaction of a corresponding methyl ketone with strong base, such as lithium diisopropyl amide.

The acids and salts derived from compounds of Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium or lithium hydroxide. The solution is stirred for an extended period of time, between 15 and 20 hours, cooled, acidified and the hydrolysate recovered by conventional means.

The amide (in Formula 1 B is $CONR_9R_{10}$) may be formed by any appropriate amidation means known in the art from the corresponding esters or carboxylic acids. One way to prepare such compounds is to convert an acid to an acid chloride and then treat that compound with ammonium hydroxide or an appropriate amine.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.,* 399, 1979), or dimethyl sulfoxide/oxalyl chloride in methylene chloride (Omura, K., Swern, D., *Tetrahedron,* 1978. 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 1 where B is H can be prepared from the corresponding halogenated aromatic compounds, preferably where the halogen is I.

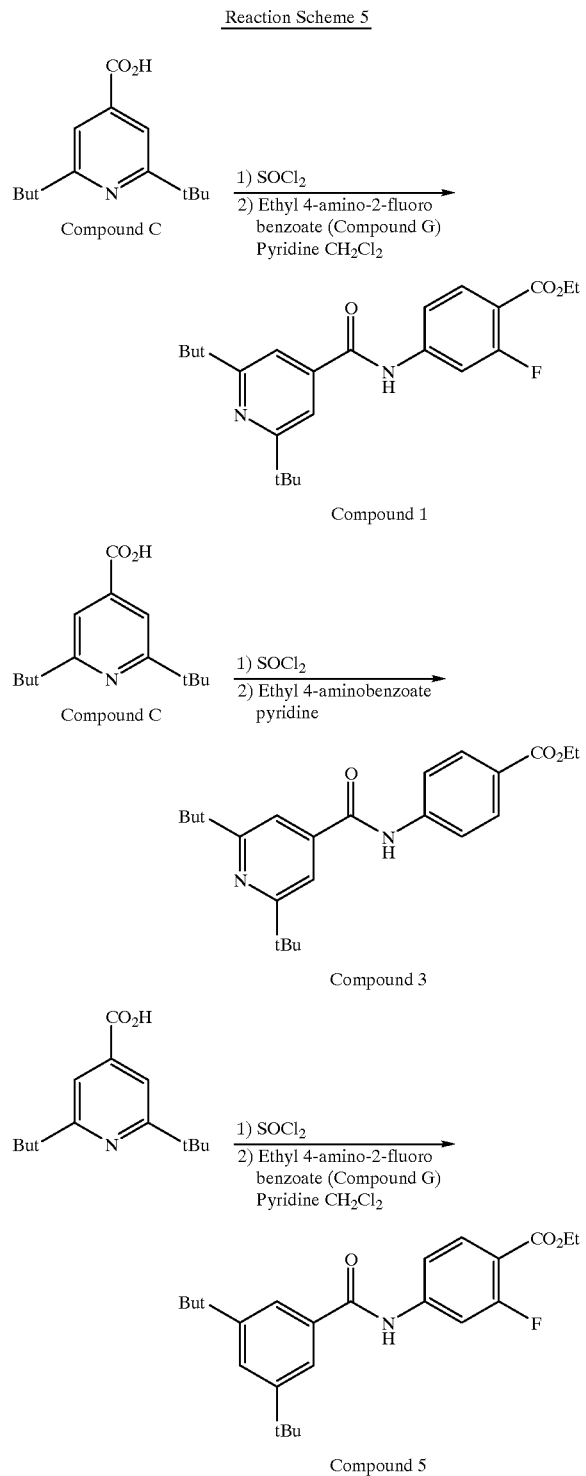

Reaction Scheme 5

Compound 1

Compound 3

Compound 5

19
-continued

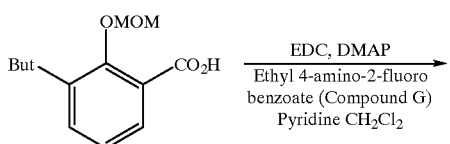

Compound F

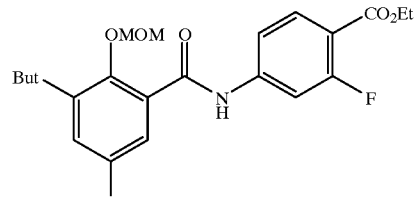

Compound N

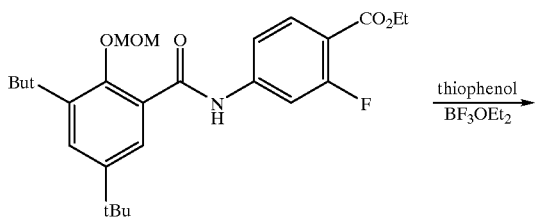

Compound N

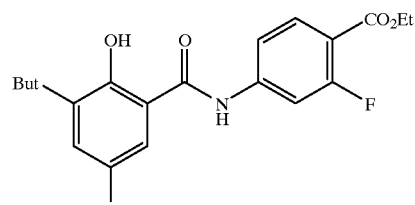

Compound 7

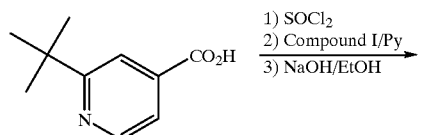

Compound C

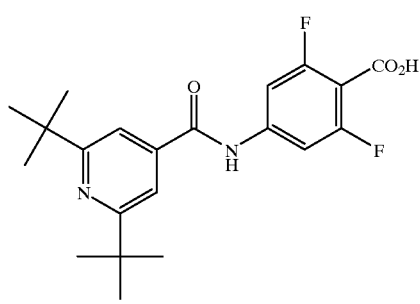

Compound 10

20
-continued

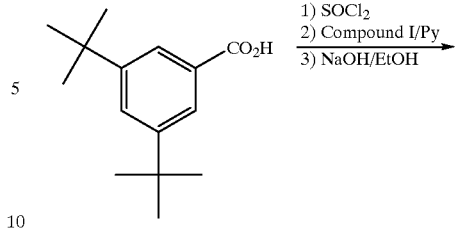

Compound 12

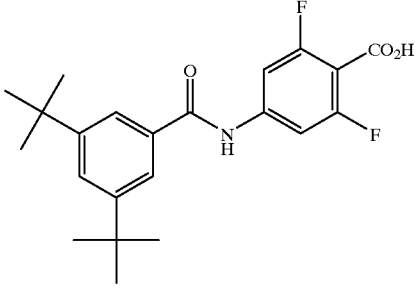

Compound C

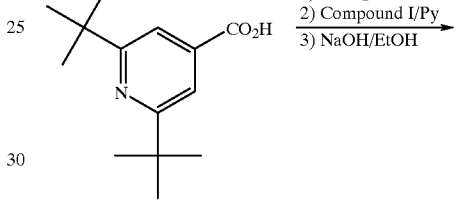

Compound 14

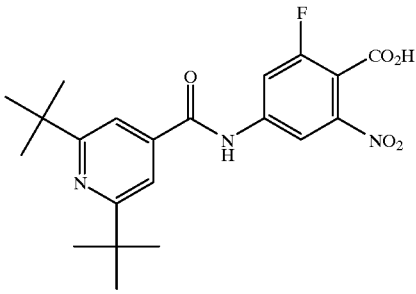

Reaction Scheme 5 illustrates examples for the formation of the carbamoyl (amide) compounds of the present invention by reaction of a reagent of Formula 2 with a reagent of Formula 3. Thus, 2,6-di-tert-butylisonicotinic acid (Compound C) is reacted with thionyl chloride ($SOCl_2$) to provide the intermediate acid chloride, which is then reacted with ethyl 2-fluoro-4-amino-benzoate (Compound G) in the presence of an acid acceptor (pyridine) to yield ethyl 2-fluoro-4-[(2'6'-di-tert-butylpyrid-4'-yl)carbamoyl] benzoate (Compound 1). As another example, 3,5-di-tert-butylbenzoic acid (available by the literature procedure of Kagechika et al., J. Med. Chem. 1988, 31, 2182, incorporated herein by reference) is reacted with thionyl chloride, followed by ethyl 2-fluoro-4-amino-benzoate (Compound G) to yield ethyl 2-fluoro-4-[(3',5'-di-tert-butylphenyl) carbamoyl]benzoate (Compound 5). As still another example, O-methoxymethyl-3,5-di-tert-butylsalicylic acid (Compound F) is reacted with ethyl 2-fluoro-4-amino-benzoate (Compound G) in the presence of 4-dimethylaminopyridine (DMAP) catalyst and 1-(3-dimethylaminopropyl)-3-ethylcarbodiimide hydrochloride (EDC) to give ethyl 2-fluoro-4-((2'-methoxymethyl-3',5'-di-tert-butylphenyl)carbamoyl]benzoate (Compound N). The methoxymethyl protecting group is removed from Compound N by treatment with borontrifluoride ethereate and thiophenol to yield ethyl 2-fluoro-4-[(2'-hydroxy-3',5'-di-tert-butylphenyl)carbamoyl]benzoate (Compound 7).

In yet another example shown in Reaction Scheme 5, 2,6-di-tert-butylisonicotinic acid (Compound C) is reacted with thionyl chloride ($SOCl_2$), the resulting intermediate acid chloride is reacted with methyl 2,6-difluoro-4-amino benzoate (Compound I), followed by saponification of the ester group, to yield 2,6-difluoro-4-[(2',6'-di-tert-butylpyrid-4'yl)carbamoyl]benzoic acid (Compound 10). 3,5-Di-tert-butylbenzoic acid is subjected to the same sequence of reactions to provide 2,6-difluoro-4-[(3',5'-di-tert-butylphenyl)carbamoyl]benzoic acid (Compound 12).

As yet another example, shown in Reaction Scheme 5, 2,6-di-tert-butylisonicotinic acid (Compound C) is reacted with thionyl chloride ($SOCl_2$), followed by methyl 2-nitro-4-aminobenzoate (Compound K) and saponification of the ester function to give 2-nitro-4-[(2',6'-di-tert-butylpyrid-4'-yl)carbamoyl]benzoic acid (Compound 14).

SPECIFIC EXAMPLES

4-Bromomethyl-2,6-di-t-butylpyridine (Compound A)

To a mixture of 2,6-di-t-butyl-4-methylpyridine (Aldrich, 2.0 g, 9.73 mmol) in 25 ml of dry $CCl_4$ was added benzoyl peroxide (24 mg, 0.097 mmol) and NBS (1.9 g, 10.7 mmol). The reaction mixture was refluxed for 16 hours. After it cooled to room temperature, the solvent was removed in vacuo and the residue was purified by column chromatography (silica gel, hexane) to give an oil (1.957 g) which contained 82% of the desired product and 18% of the starting material.

$^1$H NMR δ7.09 (s, 2H), 4.39 (s, 2H), 1.35 (s, 18H).

4-Hydroxymethyl-2,6-di-t-butylpyridine (Compound B)

A heterogeneous solution of 4-bromomethyl-2,6-di-t-butylpyridine (Compound A, 1.743 g, 82% purity) in 20 ml of 12% NaOH in water and 10 ml of 1,4-dioxane was refluxed for 12 hours. The solution spontaneously separated into two layers as it cooled to room temperature. The upper layer was separated and ethyl acetate was added. This organic layer was then washed with brine, water and dried over $MgSO_4$. The desired product was purified by column chromatography (ethyl acetate/hexane 1/9) to give a white solid.

$^1$H NMR δ7.09 (s, 2H), 4.67 (d, J=4.4 Hz, 2H), 2.3 (b, 1H), 1.36 (s, 18H).

2,6-Di-t-butylisonicotinic acid (Compound C)

Jone's reagent was added dropwise to a solution of 4-hydroxymethyl-2,6-di-t-butylpyridine (Compound B, 302 mg, 1.37 mmol) in 5 ml of acetone until the solution changed color from light yellow to orange (55 drops of Jone's reagent were consumed). After 5 minutes 2 ml of isopropanol were added to the reaction mixture, and a green precipitate of $Cr^{3+}$ salt was formed. The precipitate was removed by filtration and the solution was diluted with ethyl acetate, then washed with brine, water and dried over $MgSO_4$. After filtration, the solvent was removed to give the desired product as a white solid (227 mg).

$^1$H NMR δ7.71 (s, 2H), 1.34 (s, 18H).

2-Bromo-4,6-di-t-butylphenol (Compound D)

To a solution of 2,4-di-t-butylphenol (Aldrich, 2.0 g, 9.7 mmol) in 2 ml of HOAC was added $Br_2$ (0.5 ml, 9.7 mmol). The reaction mixture was stirred at room temperature for 12 hours. Solvent was removed under reduced pressure and the residue was purified by column chromatography (ethyl acetate/hexane 1/20) to yield the desired product (2.54 g) as a white solid.

$^1$H NMR δ7.33 (d, J=2.3 Hz, 1H), 7.24 (d, J=2.3 Hz, 1H), 1.41 (s, 9H), 1.29 (s, 9H).

O-Methoxymethyl-2-bromo-4,6-di-t-butylphenol (Compound E)

To a solution of 2-bromo-4,6-di-t-butylphenol (Compound D 2.54 g, 8.88 mmol) and catalytic amount of $Bu_4NI$ in 20 ml of dry $CH_2Cl_2$ at 0° C. was added diisopropylethylamine (9.51 ml, 53 mmol), followed by methoxymethyl chloride (2.02 ml, 26.6 mmol). The reaction mixture was heated to 45° C. for 12 hours. The reaction mixture was then washed with 10% citric acid, then $NaHCO_3$ (sat.), brine, and dried over $MgSO_4$. After filtration and removal of the solvent under reduced pressure, the residue was purified by column chromatography (pure hexane) to yield the title compound (2.79 g) as a colorless oil.

$^1$H NMR δ7.40 (d, J=2.44 Hz, 1H), 7.30 (d, J=2.4 Hz, 1H), 5.22 (s, 2H), 3.70 (s, 3H), 1.43 (s, 9H), 1.29 (s, 9H).

O-Methoxymethyl-3',5'-di-t-butylsalicylic acid (Compound F)

To a solution of o-methoxymethyl-2-bromo-4,6-di-t-butylphenol (Compound E, 2.79 g, 8.5 mmol) in 30 ml of dry THF at −78° C. under Ar was added 11 ml of t-BuLi (1.7 M in hexane, 18.7 mmol). This mixture was stirred at −78° C. for 1 hour. Then $CO_2$ (g) was bubbled into the solution at −78° C. for 1 hour. After removal of the $CO_2$ stream, the reaction mixture was stirred for an additional hour at −78° C. Then 10% of HCl was added and the mixture was allowed to warm to room temperature and extracted with ethyl acetate. The organic layer was washed with brine and dried over $Na_2SO_4$. After concentration, the residue was purified by column chromatography (ethyl acetate/hexane 1/1) to yield the title compound as a white solid (492 mg).

$^1$H NMR δ7.75 (d, J=2.81 Hz, 1H), 7.60 (d, J=2.8 Hz, 1H), 5.07 (s, 2H), 3.62 (s, 3H), 1.33 (s, 9H), 1.26 (s, 9H).

Ethyl 4-Amino-2-fluorobenzoate (Compound G)

To a mixture of 2-fluoro-4-nitrotoluene (1.0 g, 6.4 mmol, Aldrich) and $Na_2Cr_2O_7$ (2.74 g, 8.4 mmol) in 13.7 ml of HOAC was added slowly 6.83 ml of $H_2SO_4$. This mixture was slowly heated to 90° C. for 1 hour to give a greenish heterogeneous solution. The mixture was cooled to room temperature and diluted with ethyl acetate. The pH of the solution was adjusted to 4 with aqueous NaOH. The mixture was extracted with more ethyl acetate. The combined organic layers were washed with $NaHCO_3$ (sat.), then brine and dried over $Na_2SO_4$. After filtration, the solution was concentrated to dryness which then was dissolved in 6 ml of $SOCl_2$, and heated at 80° C. for 1 hour. The excess of $SOCl_2$ was removed under reduced pressure and the residue was dissolved in 5 ml of $CH_2Cl_2$, 2 ml of EtOH and 2 ml of pyridine. The mixture was stirred at room temperature for 2 hours and concentrated to dryness. Ethyl 2fluoro-4-nitrobenzoate was obtained as a white solid after column chromatography of the residue with ethyl acetate/hexane (1/9). This solid was then dissolved in 10 ml of ethyl acetate, and Pd/C (50 mg) was added. Hydrogenation converted ethyl 2-fluoro-4-nitrobenzoate into the title compound.

$^1$H NMR $\delta$7.77 (t, J=8.4 Hz, 1H), 6.41 (dd, J$_1$=8.6, J$_2$=2.2 Hz, 1H), 6.33 (dd, J$_1$=13.0, J$_2$=2.2 Hz, 1H), 4.33 (q, J=7.1 Hz, 2H), 4.3 (b, 2H), 1.37 (t, J=7.1 Hz, 3H).

Methyl 4-Amino-2,6-difluorobenzoate (Compound I)

A solution of trifluorobenzoic acid (150 mg, 0.85 mmol, Aldrich) in 0.5 ml of SOCl$_2$ was heated under reflux for 2 hours. The reaction mixture was cooled to room temperature, and excess of SOCl$_2$ was removed under reduced pressure. The residue was dissolved in 1 ml of pyridine and 0.2 ml of methanol. After stirring at room temperature for 30 min, solvent was removed and the residue was purified by column chromatography (ethyl acetate/hexane 1/10) to give methyl trifluorobenzoate as a colorless oil. This oil was then dissolved in 1 ml of CH$_3$CN, then a solution of NaN$_3$ (100 mg, 1.54 'mol) in 0.5 ml of water was added. The reaction mixture was refluxed for two days. Salt was removed by filtration and the remaining solution was concentrated to an oil. This oil was then dissolved in 1 ml of methanol, followed by a catalytic amount of Pd/C (10%, w/w). The reaction mixture was hydrogenated for 12 hours. Catalyst was removed and the solution was concentrated to an oil. After column chromatography (ethyl acetate/hexane 1/3), the title compound was obtained as colorless crystals.

$^1$H NMR $\delta$6.17 (d, J=10.44 Hz, 2H), 4.2 (b, 2H), 3.87 (s, 3H).

Methyl 2-Nitro-4-aminobenzoate (Compound K)

2-Nitro-4-aminobenzoic acid (261 mg, 1.43 mmol) was dissolved in 1 ml of SOCl$_2$. The solution was refluxed for 1 hour. Excess SOCl$_2$ was removed under reduced pressure and 5 ml of CH$_2$Cl$_2$, 1 ml of MeOH and TEA (0.24 ml, 1.7 mmol) were added to the residue. The reaction mixture was stirred at room temperature for 2 hours. Excess MeOH and TEA were removed and the residue was purified by column chromatography with ethyl acetate/hexane (1/3) to yield the title compound as a yellow solid (316 mg).

$^1$H NMR $\delta$7.69 (d, J=8.5 Hz, 1H), 6.85 (d, J=2.2 Hz, 1H), 6.67 (dd, J=8.3; 2.1 Hz, 1H), 4.31 (b, 2H), 3.94 (s, 3H).

Ethyl 2-fluoro-4-[(2'6'-di-t-butylpyrid-4'-yl) carbamoyl]benzoate (Compound 1)

A solution of 2,6-di-t-butylisonicotinic acid (Compound C, 47.3 mg, 0.20 mmol) in 2 ml of SOCl$_2$ was heated under reflux for 2 hours. Excess SOCl$_2$ was removed in vacuo and the residue was dissolved in 2 ml of dry CH$_2$Cl$_2$, and ethyl 2-fluoro-4-aminobenzoate (Compound G, 40.2 mg, 0.22 mmol) and pyridine (0.0835 ml, 0.69 mmol) were added. The reaction mixture was stirred at room temperature for 12 hours. Solvent was removed and the residue was purified by column chromatography (ethyl acetate/hexane 1/9) to yield the title compound (71.2 mg) as white crystals.

$^1$H NMR $\delta$8.56 (b, 1H), 7.91 (t, J=8.36 Hz, 1H), 7.53 (dd, J=12.82, 2.0 Hz, 1H), 7.39 (dd, J=8.7, 2.0 Hz, 1H), 4.33 (q, J=7.1 Hz, 2H), 1.37 (t, J=7.1 Hz, 3H), 1.35 (s, 18H).

Ethyl 4-[(2',6'-di-t-butylpyrid-4'-yl)carbamoyl] benzoate (Compound 3)

Using the same procedure as for the synthesis of ethyl 2-fluoro-4-[(2'6'-di-t-butylpyrid-4'-yl)carbamoyl]benzoate (Compound 1) but using 2,6-di-t-butylisonicotinic acid (Compound C, 101 mg, 0.43 mmol) and ethyl 4-aminobenzoate (78 mg, 0.47 mmol), the title compound was obtained as a white solid (135 mg).

$^1$H NMR $\delta$8.43 (b, 1H), 8.02 (d, J=8.7 Hz, 2H), 7.75 (d, J=8.7 Hz, 2H), 7.48 (s, 2H), 4.33 (q, J=7.1 Hz, 2H), 1.38 (t, J=7.1 Hz, 3H), 1.35 (s, 18H).

Ethyl 2-Fluoro-4-[(3',5'-di-t-butylphenyl)carbamoyl] benzoate (Compound 5)

Using the same procedure as for the synthesis of ethyl 2-fluoro-4-[(2'6'-di-t-butylpyrid-4'-yl)carbamoyl]benzoate (Compound 1) but using 3,5-di-t-butylbenzoic acid (60 mg, 0.26 mmol, available by literature procedure, see Kagechika et al. J. Med Chem. 1988 31, 2182–2192) and ethyl 2-fluoro-4-aminobenzoate (Compound G, 51.5 mg, 0.28 mmol), the title compound was obtained as a white solid (66 mg).

$^1$H NMR $\delta$8.21 (b, 1H), 7.93 (t, J=8.3 Hz, 1H), 7.79 (dd, J=12.8, 2.0 Hz, 1H), 7.67 (d, J=1.8 Hz, 2H), 7.65 (t, J=1.7 Hz, 1H), 7.35 (dd, J=8.7, 2.1 Hz, 1H), 4.36 (q, J=7.2 Hz, 2H), 1.39 (t, J=7.2 Hz, 3H), 1.36 (s, 18H).

Ethyl 2-Fluoro-4-[(2'-methoxymethyl-3',5'-di-t-butylphenyl)carbamoyl]benzoate (Compound N)

To a mixture of O-methoxymethyl-3',5'-di-t-butylsalicylic acid (Compound F, 150 mg, 0.51 mmol), 4-dimethylaminopyridine (142 mg, 0.61 mmol) and ethyl 2-fluoro-4-aminobenzoate (Compound G, 102 mg, 0.56 mmol) in 5 ml of dry CH$_2$Cl$_2$ was added 1-(3-di-methylaminopropyl)-3-ethylcarbodiimide hydrochloride (117 mg, 0.61 mmol). The reaction mixture was stirred at room temperature for 12 hours. Solvent was evaporated in vacuo and the residue was dissolved in ethyl acetate, then washed with brine, water and dried over MgSO$_4$. After filtration, solvent was removed and the residue was purified by column chromatography (ethyl acetate/hexane 1/3) to give the title compound (58 mg).

$^1$H NMR $\delta$8.97 (b, 1H), 7.94 (t, J=8.37 Hz, 1H), 7.78 (d, J=2.7 Hz, 1H), 7.61 (d, J=13.0 Hz, 1H), 7.56 (d, J=2.6 Hz, 1H), 7.35 (d, J=8.7 Hz, 1H), 5.00 (s, 2H), 3.53 (s, 3H), 4.38 (q, J=7.1 Hz, 2H), 1.47 (s, 9H), 1.39 (t, J=7.2 Hz, 3H), 1.33 (s, 9H).

Ethyl 2-Fluoro-4-[(2'-hydroxy-3',5'-di-t-butylphenyl) carbamoyl]benzoate (Compound 7)

To a solution of ethyl 2-fluoro-4-[(2'-methoxymethyl-3', 5'-di-t-butylphenyl)carbamoyl]benzoate (Compound N, 34 mg, 0.07 mmol) in 1 ml of THF were added 10 drops of HOAC. The reaction mixture was heated to reflux for 12 hours. Solvent was removed and ethyl acetate was added. The solution was washed with NaCHO$_3$ (sat.), brine, water and dried over MgSO$_4$. Solvent was removed in vacuo to give an oil. The oil was allowed to be exposed to the atmosphere for 12 hours during which time crystals formed. The crystals were collected and washed several times with hexane to afford the title compound as a white solid (13.5 mg).

$^1$H NMR $\delta$10.73 (s, 1H), 7.98 (d, J=2.56 Hz, 1H), 7.88 (b, 1H), 7.75 (t, J=8.26 Hz, 1H), 7.60 (d, J=2.44 Hz, 1H), 7.32 (dd, J=12.3, 2.0 Hz, 1H), 7.02 (dd, J=8.6, 2.0 Hz, 1H), 4.35 (q, J=7.2 Hz, 2H), 1.39 (s, 9H), 1.37 (t, J=7.2 Hz, 3H), 1.5 (s, 9H).

2, 6-Difluoro-4-[(2',6'-di-t-butylpyrid-4'yl) carbamoyl]benzoic Acid (Compound 10)

To 2,6-di-t-butylisonicotinic acid (Compound C, 20 mg, 0.085 mmol) was added 1 ml of SOCl$_2$. The mixture was heated under reflux for 2 hours. After cooling to room temperature, excess $SOCl_2$ was removed and the residue was dissolved in 2 ml of $CH_2Cl_2$. To this solution was added methyl 2,6-difluoro-4-aminobenzoate (Compound I, 16 mg, 0.085 mmol) and triethylamine (0.015 ml, 0.1 mmol). The reaction mixture was kept at room temperature for 2 hours and then concentrated to dryness. The residue was purified by column chromatography with ethyl acetate/hexane (1/10) to yield the methyl ester of the title compound. This was saponified according to the general procedure (see below) to give the title compound as a colorless solid.

$^1$H NMR δ7.44 (s, 2H), 7.40 (d, J=11.8 Hz, 2H) 1.37 (s, 18H)

2,6-Difluoro-4-[(3',5'-di-t-butylphenyl)carbamoyl]benzoic Acid (Compound 12)

Using the same procedure as for the preparation of 2,6-difluoro-4-[(2',6'-di-t-butylpyrid-4'yl)carbamoyl]benzoic acid (Compound 10) but using 3,5-di-t-butylbenzoic acid (37 mg, 0.16 mmol) and methyl 2,6-difluoro-4-aminobenzoate (Compound I, 29 mg, 0.16 mmol), the title compound was obtained as colorless crystals.

1H NMR δ7.92 (b, 1H) 7.60 (m, 3H), 7.42 (d, J=10.0 Hz, 2H), 1.38 (s, 18H).

2-Nitro-4-[(2',6'-di-t-butylpyrid-4'-yl)carbamoyl]benzoic Acid (Compound 14)

Using the same procedure as for the preparation of 2,6-difluoro-4-[(2',6'-di-t-butylpyrid-4'yl)carbamoyl]benzoic acid (Compound 10) but using 2,6-di-t-butylisonicotinic acid (40 mg, 0.17 mmol) and methyl 2-nitro-4-aminobenzoate (Compound K, 33 mg, 0.17 mmol), the title compound was obtained as a light yellow oil.

$^1$H NMR δ(acetone-d$^6$) 10.25 (b, 1H), 8.32 (s, 1H), 7.97 (d, J=8.1 Hz, 1H), 7.93 (b, 1H), 7.70 (s, 2H), 1.36 (s, 18H).

General Procedure for the Syntheses of Benzoic Acid Derivatives by Hydrolyzing the Corresponding Methyl or Ethyl Esters To a solution of ester (3.0 mmol) in 20 ml of EtOH was added 5 ml of 1 N NaOH in water. The reaction mixture was stirred at room temperature for overnight and neutralized with 10% HCl to PH=5. The alcohol was removed by evaporation and the aqueous layer was extracted with ethyl acetate (3×10 ml). The ethyl acetate layer was further washed with $NaHCO_3$ (sat.), brine and dried over $MgSO_4$. After concentration, the desired carboxylic acid was obtained which could be recrystallized in ethyl acetate or acetonitrile.

2-Fluoro-4-[(2',6'-di-t-butylpyrid-4'-yl)carbamoyl]benzoic Acid (Compound 2)

$^1$H NMR δ($CD_3OD$) 7.92 (t, J=8.36 Hz, 1H), 7.82 (dd, J=12.82, 2.0 Hz, 1H), 7.63 (s, 2H), 7.55 (dd, J=8.7, 2.1 Hz, 1H), 1.39 (s, 18H).

4-[(2',6'-Di-t-butylpyrid-4'-yl)carbamoyl]benzoic acid (Compound 4)

$^1$H NMR δ($CD_3OD$) 8.02 (d, J=8.85 Hz, 2H), 7.85 (d, J=8.85 Hz, 2H), 7.63 (s, 2H), 1.40 (s, 18H).

2-Fluoro-4-[(3',5'-di-t-butyl1phenylcarbamoyl]benzoic acid (Compound 6)

$^1$H NMR δ($CD_3OD$) 7.92 (t, J=8.3 Hz, 1H), 7.80 (dd, J=12.8, 2.0 Hz, 1H), 7.79 (d, J=1.8 Hz, 2H), 7.69 (t, J=1.7 Hz, 1H), 7.57 (dd, J=8.7, 2.1 Hz, 1H), 1.37 (s, 18H).

2-Fluoro-4-[(2'-hydroxy-3',5'-di-t-butyl)phenylcarbamoyl]benzoic acid (Compound 8)

$^1$H NMR δ (acetone-d$_6$) 12.3 (b, 1H), 10.07 (b, 1H), 7.98 (t, J=8.48 Hz, 1H), 7.80 (m, 2H), 7.58 (d, J=2.3 Hz, 1H), 7.56 (dd, J=8.8, 2.0 Hz, 1H), 1.44 (s, 9H), 1.31 (s, 9H).

What is claimed is:

1. A compound of the formula

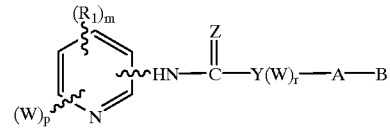

wherein $R_1$ is independently H or alkyl of 1 to 6 carbons;

m is an integer having the value of 0–5;

p is an integer having the value of 0–2;

r is an integer having the value 0–2;

Z is O or S;

Y is a naphthyl group, or heteroaryl selected from a group consisting of pyridazinyl, pyrimidinyl, thiazolyl, oxazolyl, imidazolyl and pyrrazolyl, said naphthyl and heteroaryl groups being optionally substituted with one or two $R_1$ groups;

W is a substituent selected independently from the group consisting of F, Br, Cl, I, $C_{1-6}$alkyl, fluoro substituted $C_{1-6}$ alkyl, $NO_2$, $N_3$, OH, $OCH_2OCH_3$, $OC_{1-10}$alkyl, tetrazol, CN, $SO_2C_{1-6}$-alkyl, $SO_2C_{1-6}$-fluoro substituted alkyl, SO-$C_{1-6}$ alkyl, CO-$C_{1-6}$alkyl, $COOR_8$, phenyl, phenyl itself substituted with a W group other than with phenyl or substituted phenyl;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is COOH or a pharmaceutically acceptable salt thereof, $COOR_8$, $CONRR_{10}$, $-CH_2OH$, $CH_2OR_{11}$, $CH_2OCOR_{11}$, CHO, $CH(OR_{12})_2$, $CHOR_{13}O$, $-COR_7$, $CR_7OR_{12})_2$, $CR_7OR_{13}O$, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

2. A compound in accordance with claim 1 where Y is pyridazinyl.

3. A compound in accordance with claim 2 where Z is O.

4. A compound in accordance with claim 1 where Y is pyrimidinyl.

5. A compound in accordance with claim 4 where Z is O.

6. A compound in accordance with claim 1 where Y is thiazolyl.

7. A compound in accordance with claim 6 where Z is O.

8. A compound in accordance with claim 1 where Y is selected from the group consisting of oxazolyl, imidazolyl and pyrrazolyl.

9. A compound in accordance with claim 8 where Z is O.

10. A compound in accordance with claim 1 where Y is naphthyl.

11. A compound in accordance with claim 8 where Z is O.

12. A compound of the formula

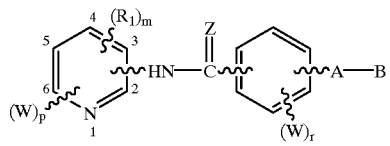

wherein $R_1$ is independently H or alkyl of 1 to 6 carbons;
m is an integer having the value of 0–5;
p is an integer having the value of 0–2;
r is an integer having the value 0–2;
Z is O or S;
W is a substituent selected independently from the group consisting of F, Br, Cl, I, $C_{1-6}$alkyl, fluoro substituted $C_{1-6}$ alkyl, $NO_2$, $N_3$, OH, $OCH_2CH_3$, $OC_{1-10}$alkyl, tetrazo CN, $SO_2C_{1-6}$-alkyl, $SO_2C_{1-6}$-fluoro substituted alkyl, SO—$C_{1-6}$ alkyl CO-$C_{1-6}$alkyl, $COOR_8$, phenyl, phenyl itself substituted with a W group other than with phenyl or substituted phenyl;
A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and
B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, with the proviso that the —NH—CO— group is attached to 2 or 4 or 5 or 6 position of the pyridine ring.

13. A compound in accordance with claim 12 where Z is O.

* * * * *

UNITED STATES PATENT AND TRADEMARK OFFICE
CERTIFICATE OF CORRECTION

PATENT NO. : 6,320,047 B1
DATED : November 20, 2002
INVENTOR(S) : Teng et al.

It is certified that error appears in the above-identified patent and that said Letters Patent is hereby corrected as shown below:

Title page,
Item [56], U.S. PATENT DOCUMENTS, "Shrool" should be -- Shroot --.

FOREIGN PATENT DOCUMENTS, "0098521" should be -- 0098591 --.

OTHER PUBLICATIONS, "Dineyl" should be -- Diaryl --; and "| 2,3-g |" should be -- [2,3-g] --.

Column 3,
Line 3, "where S is O" should be -- where Z is O --.
Line 13, "$OCH_2OCH_{31}$" should be -- $OCH_2OCH_3$, --.
Line 17, "r is O" should be -- r is 0 --.
Line 19, "$(CH_2)$" should be -- $(CH_2)_q$ --.

Column 4,
Line 20, "-COX," should be -- $-COX_1$ --.

Column 6,
Line 50, "(sara)" should be -- (para) --.

Column 9,
Lines 14 and 21, "C." should be -- C --.
Table 2, "Kagechikaetal." should be -- Kagechika et al. --.

Column 10,
Lines 19 and 51, "C." should be -- C --.
Line 36, "Iscovels" should be -- Iscove's --.

Column 11,
Line 3, "C." should be -- C --.

Column 13,
Line 45, "(MOMCl)to" should be -- (MOMCl) to --.

UNITED STATES PATENT AND TRADEMARK OFFICE
CERTIFICATE OF CORRECTION

PATENT NO. : 6,320,047 B1
DATED : November 20, 2002
INVENTOR(S) : Teng et al.

It is certified that error appears in the above-identified patent and that said Letters Patent is hereby corrected as shown below:

Column 14,
Line 8, Reaction Scheme 2, above the, "C." should be -- C --.

Column 15,
Line 25, Reaction Scheme 3, Formula 2a,

Line 36, "($X_1$=Cl)" should be -- ($X_1$ = Cl) --.

Column 17,
Line 4, "Mcomie" should be -- McOmie --.

Column 18,
Lines 50-55, Reaction Scheme 5, the unlabelled compound,

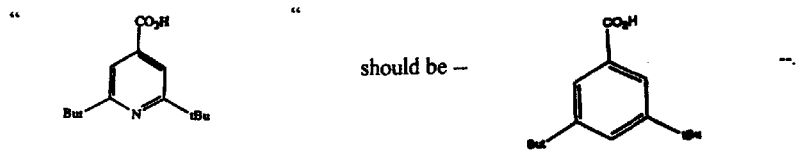

Column 20,
Line 65, "(Compound F)is" should be -- (Compound F) is --.

Column 21,
Line 3, "2-fluoro-4-((2'" should be -- 2-fluoro-4-[(2' --.
Lines 40 and 55, "δ7.09" should be -- δ 7.09 --.

UNITED STATES PATENT AND TRADEMARK OFFICE
CERTIFICATE OF CORRECTION

PATENT NO. : 6,320,047 B1
DATED : November 20, 2002
INVENTOR(S) : Teng et al.

It is certified that error appears in the above-identified patent and that said Letters Patent is hereby corrected as shown below:

Column 22,
Line 3, "δ7.71" should be -- δ 7.71 --.
Line 14, "δ7.33" should be -- δ 7.33 --.
Lines 21, 24, 39, 41, 42, 57 and 65, "C." should be -- C --.
Line 31, "δ7.40" should be -- δ 7.40 --.
Line 37, "o-methoxymethyl" should be -- O-methoxymethyl --.
Line 50, "δ7.75" should be -- δ 7.75 --.

Column 23,
Line 2, "2fluoro" should be -- 2-fluoro --.
Line 8, "δ7.77" should be -- δ 7.77 --.
Line 23, "'mol" should be -- mmol --.
Line 33, "δ6.17" should be -- δ 6.17 --.
Line 45, "δ7.69" should be -- δ 7.69 --.
Line 60, "δ8.56" should be -- δ8.56 --.

Column 24,
Line 5, "δ8.43" should be -- δ 8.43 --.
Line 18, "δ8.21" should be -- δ 8.21 --.
Line 38, "δ8.97" should be -- δ 8.97 --.
Line 49, "HOAC" should be -- HOAc --.
Line 58, "δ10.73" should be -- δ 10.73 --.

Column 25,
Line 12, "δ7.44" should be -- δ 7.44 --.
Line 23, "1H NMR δ7.92" should be -- $^1$H NMR δ 7.92 --.
Line 63, "butyl1phenylcarbamoyl" should be -- butyl)phenylcarbamoyl --.

Column 26,
Line 40, "CONRR$_{10}$" should be -- CONR$_9$R$_{10}$ --.
Line 42, "CR$_7$OR$_{12}$)$_2$" should be -- CR$_7$(OR$_{12}$)$_2$ --.

UNITED STATES PATENT AND TRADEMARK OFFICE
CERTIFICATE OF CORRECTION

PATENT NO.   : 6,320,047 B1
DATED        : November 20, 2002
INVENTOR(S)  : Teng et al.

It is certified that error appears in the above-identified patent and that said Letters Patent is hereby corrected as shown below:

Column 27,
Line 18, "OCH$_2$CH$_3$" should be -- OCH$_2$OCH$_3$ --.
Line 19, "tetrazo" should be -- tetrazol, --.
Line 20, "alkyl CO" should be -- alkyl, CO --.

Signed and Sealed this

Sixth Day of May, 2003

JAMES E. ROGAN
*Director of the United States Patent and Trademark Office*